(12) United States Patent
Zeller

(10) Patent No.: US 6,194,611 B1
(45) Date of Patent: *Feb. 27, 2001

(54) N-SULPHONYL AND N-SULPHINYL AMINO ACID DERIVATIVES AS MICROBICIDES

(75) Inventor: Martin Zeller, Baden (CH)

(73) Assignee: Novartis Crop Protection, Inc., Greensboro, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,688
(22) PCT Filed: Oct. 7, 1996
(86) PCT No.: PCT/EP96/04349
  § 371 Date: Apr. 16, 1998
  § 102(e) Date: Apr. 16, 1998
(87) PCT Pub. No.: WO97/14677
  PCT Pub. Date: Apr. 24, 1997

(30) Foreign Application Priority Data

Oct. 18, 1995 (CH) .................................................. 2957/95
Jul. 9, 1996 (CH) .................................................. 1716/96

(51) Int. Cl.$^7$ ........................ C07C 331/00; C07C 381/00
(52) U.S. Cl. ................................ 564/79; 564/80; 564/99; 564/100; 564/189; 564/191; 564/196; 548/542; 560/9; 560/13
(58) Field of Search ................................ 564/79, 80, 99, 564/100, 189, 191, 196; 548/542; 560/9, 13

(56) References Cited

U.S. PATENT DOCUMENTS 5,482,972   1/1996   Seitz et al. .
5,585,519 * 12/1996   Zeller .

FOREIGN PATENT DOCUMENTS 0 493 683    7/1992   (EP) .
0 554 729    8/1993   (EP) .
WO 95/30651  11/1995  (WO) .

* cited by examiner

Primary Examiner—James O. Wilson

(74) Attorney, Agent, or Firm—William A. Teoli, Jr.

(57) ABSTRACT

α-Amino acid amides of formula (I) wherein the substituents are defined as follows: n is the number zero or one; $R_1$ to $R_7$ are as herein defined; $R_8$ is $C_1$–$C_6$alkyl, $C_3$–$C_6$alkenyl or $C_3$–$C_6$alkynyl; $R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group (a) wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$cycloalkyl, $C_1$–$C_6$haloalcoxy, $C_1$–$C_6$alkylthio, $C_1$–$C_6$alcoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; —$COOR_{17}$; —$COR_{18}$ or a group (b) wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_2$–$C_6$alkenyl, $C_2$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl, are valuable microbicides. They can be used in plant protection in the form of suitable compositions, for example in the control of fungal diseases.

18 Claims, No Drawings

N-SULPHONYL AND N-SULPHINYL AMINO ACID DERIVATIVES AS MICROBICIDES

The present invention relates to novel a-amino acid amides of formula I below. It relates to the preparation of those substances and to agrochemical compositions that comprise at least one of those compounds as active ingredient The invention also relates to the preparation of the said compositions and to the use of the active ingredients or the compositions in the control or prevention of plant infestation by phytopathogenic microorganisms, especially fungi.

The compounds according to the invention correspond to the general formula I

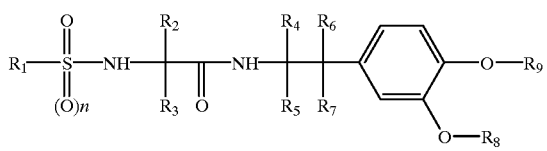

wherein the substituents are defined as follows:

n is the number zero or one;

$R_1$ is $C_1$–$C_{12}$alkyl that is unsubstituted or may be substituted by $C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or by $C_3$–$C_6$alkynyloxycarbonyl; $C_3$–$C_8$cycloalkyl; $C_2$–$C_{12}$alkenyl; $C_2$–$C_{12}$-alkynyl; $C_1$–$C_{12}$haloalkyl or a group $NR_{11}R_{12}$, wherein $R_{11}$ and $R_{12}$ are each independently of the other hydrogen or $C_1$–$C_6$alkyl, or together are tetramethylene or pentamethylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$-alkynyl or $C_3$–$C_8$cycloalkyl-$C_1$–$C_4$alkyl; or the two groups $R_2$ and $R_3$ together with the carbon atom to which they are bonded form a three- to eight-membered carbocyclic ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

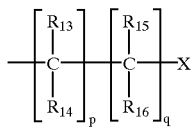

wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; —$COOR_{17}$; —$COR_{18}$ or a group

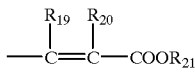

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_2$–$C_6$alkenyl, $C_2$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl.

A preferred group is formed by compounds of formula I

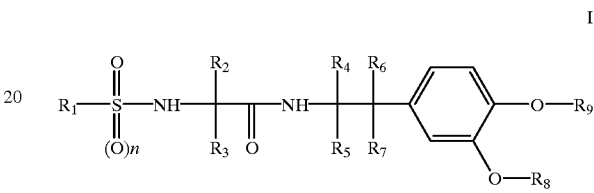

wherein the substituents are defined as follows:

n is the number zero or one;

$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or by $C_3$–$C_6$alkynyloxycarbonyl; $C_3$–$C_8$cycloalkyl; $C_2$–$C_{12}$alkenyl; $C_2$–$C_{12}$-alkynyl; $C_1$–$C_{12}$haloalkyl or a group $NR_{11}R_{12}$, wherein $R_1$ and $R_{12}$ are each independently of the other hydrogen or $C_1$–$C_6$alkyl, or together are tetramethylene or pentamethylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$-alkynyl or $C_3$–$C_8$cycloalkyl-$C_1$–$C_4$alkyl; or the two groups $R_2$ and $R_3$ together with the carbon atom to which they are bonded form a three- to eight-membered carbocyclic ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

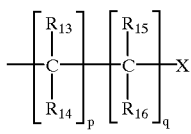

wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or substituted by halogen, nitro, cyano, $C_1$–$C_4$alkyl or by $C_1$–$C_4$alkoxy; cyano; —$COOR_{17}$; —$COR_{18}$ or a group

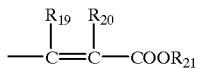

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (subgroup 1A).

An important group is formed by compounds of formula I wherein n is the number one;

$R_1$ is $C_1$–$C_{12}$alkyl that is unsubstituted or may be substituted by $C_1$–$C_4$alkoxy, $C_1$–$C_4$alkylthio or by $C_1$–$C_4$alkylsulfonyl; $C_2$–$C_{12}$alkenyl; $C_2$–$C_{12}$alkynyl; $C_1$–$C_{12}$haloalkyl or a group $NR_{11}R_{12}$, wherein $R_{11}$ and $R_{12}$ are each independently of the other hydrogen or $C_1$–$C_6$-alkyl, or together are tetramethylene or pentamethylene;

$R_2$ is hydrogen; and $R_3$ is $C_1$–$C_8$alkyl; $C_1$–$C_8$alkyl substituted by hydroxy, $C_1$–$C_4$alkoxy, mercapto or by $C_1$–$C_4$-alkylthio; $C_3$–$C_8$alkenyl; $C_3$–$C_8$alkynyl or $C_3$–$C_8$cycloalkyl-$C_1$–$C_4$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

$R_9$ is $C_3$–$C_6$cycloalkyl; a $C_1$–$C_6$alkyl, $C_3$–$C_6$alkenyl or $C_3$–$C_6$alkynyl group substituted by one or more halogen atoms; or a group

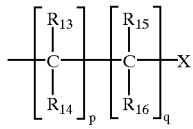

wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or substituted by halogen, nitro, cyano, $C_1$–$C_4$alkyl or by $C_1$–$C_4$alkoxy; cyano; —$COOR_{17}$; —$COR_{18}$ or a group

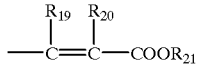

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$allyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (subgroup A).

An important group is formed by compounds of formula I wherein n is the number one;

$R_1$ is $C_1$–$C_{12}$alkyl that is unsubstituted or may be substituted by $C_1$–$C_4$alkoxy, $C_1$–$C_4$alkylthio or by $C_1$–$C_4$alkylsulfonyl; $C_2$–$C_{12}$alkenyl; $C_2$–$C_{12}$alkynyl; $C_1$–$C_{12}$haloalkyl or a group $NR_{11}R_{12}$, wherein $R_{11}$ and $R_{12}$ are each independently of the other $C_1$–$C_6$alkyl, or together are tetramethylene or pentamethylene;

$R_2$ is hydrogen; and $R_3$ is $C_1$–$C_8$alkyl; $C_1$–$C_8$alkyl substituted by hydroxy, $C_1$–$C_4$alkoxy, mercapto or by $C_1$–$C_4$-alkylthio; $C_3$–$C_8$alkenyl; $C_3$–$C_8$alkynyl or $C_3$–$C_8$cycloalkyl-$C_1$–$C_4$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

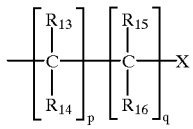

wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or substituted by halogen, nitro, cyano, $C_1$–$C_4$alkyl or by $C_1$–$C_4$alkoxy; cyano; —$COOR_{17}$; —$COR_{18}$ or a group

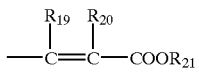

wherein $R_{17}$ and $R_{21}$ are each independently of the other hydrogen, $C_1$–$C_6$alkyl. $C_3$–$C_6$alkenyl or $C_3$–$C_6$alkynyl, and $R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (subgroup B).

Of special importance are compounds of formula I wherein n is the number one;

$R_1$ is $C_1$–$C_{12}$alkyl; $C_1$–$C_{12}$haloalkyl or a group $NR_1R_{12}$, wherein $R_{11}$ and $R_{12}$ are $C_1$–$C_6$-alkyl;

$R_2$ is hydrogen; and $R_3$ is $C_1$–$C_8$alkyl;

$R_4$ is hydrogen or $C_1$–$C_4$alkyl;

$R_5$, $R_6$ and $R_7$ are hydrogen;

$R_8$ is $C_1$–$C_6$alkyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

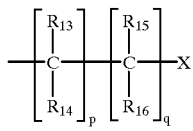

wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or substituted by halogen, nitro, cyano, $C_1$–$C_4$alkyl or by $C_1$–$C_4$alkoxy; cyano; —$COOR_{17}$; —$COR_{18}$ or a group

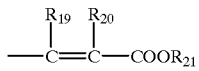

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (subgroup Ba).

Another important group is formed by compounds of formula I wherein n is the number one;

$R_1$ is $C_1$–$C_4$alkyl or dimethylamino;

$R_2$ is hydrogen; and $R_3$ is $C_3$–$C_4$alkyl;

$R_4$ is hydrogen or methyl;

$R_5$, $R_6$ and $R_7$ are hydrogen;

$R_8$ is $C_1$–$C_2$alkyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

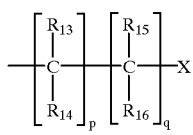

wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or substituted by halogen, nitro, cyano, $C_1$–$C_4$alkyl or by $C_1$–$C_4$alkoxy; cyano; —$COOR_{17}$; —$COR_{18}$ or a group

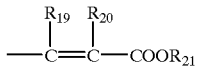

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (subgroup Bb).

Preferred among those groups are those wherein n is the number one;

$R_1$ is $C_2$–$C_4$alkyl or dimethylamino;

$R_2$ is hydrogen; and $R_3$ is 2-propyl;

$R_4$ is hydrogen;

$R_5$, $R_6$ and $R_7$ are hydrogen;

$R_8$ is methyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

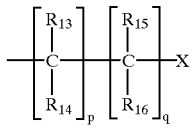

wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or substituted by halogen, nitro, cyano, $C_1$–$C_4$alkyl or by $C_1$–$C_4$alkoxy; cyano; —$COOR_{17}$; —$COR_{18}$ or a group

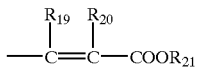

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (subgroup Bc).

Another preferred group is formed by compounds of formula I wherein n is the number one;

$R_1$ is $C_1$–$C_{12}$alkyl that is unsubstituted or may be substituted by $C_1$–$C_4$alkoxy, $C_1$–$C_4$alkylthio or by $C_1$–$C_4$alkylsulfonyl; $C_2$–$C_{12}$alkenyl; $C_2$–$C_{12}$alkynyl; $C_1$–$C_{12}$haloalkyl or a group $NR_{11}R_{12}$, wherein $R_{11}$ and $R_{12}$ are each independently of the other $C_1$–$C_6$alkyl, or together are tetramethylene or pentamethylene;

$R_2$ is hydrogen; and $R_3$ is $C_1$–$C_8$alkyl; $C_1$–$C_8$alkyl substituted by hydroxy, $C_1$–$C_4$alkoxy, mercapto or by $C_1$–$C_4$-alkylthio; $C_3$–$C_8$alkenyl; $C_3$–$C_8$alkynyl or $C_3$–$C_8$cycloalkyl-$C_1$–$C_4$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

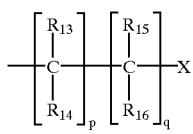

wherein p is the number zero or one; and q is the number zero; and $R_{13}$ and $R_{14}$ are identical or different and are each independently of the other hydrogen or $C_1$–$C_4$alkyl; and X is hydrogen, in which case p must have the value zero; phenyl unsubstituted or substituted by halogen, nitro, cyano, $C_1$–$C_4$alkyl or by $C_1$–$C_4$alkoxy; cyano; —COOR$_{17}$; —COR$_{18}$ or a group

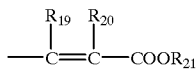

wherein $R_{17}$ and $R_{21}$ are $C_1$–$C_6$alkyl, and $R_{18}$ is hydrogen; $C_1$–$C_6$alkyl or phenyl, unsubstituted or substituted by halogen, nitro, cyano, $C_1$–$C_4$alkyl or by $C_1$–$C_4$alkoxy, and $R_{19}$ and $R_{20}$ are hydrogen (sub-group C).

Important compounds of sub-group C within the scope of formula I are those wherein n is the number one;

$R_1$ is $C_1$–$C_{12}$alkyl that is unsubstituted or may be substituted by $C_1$–$C_4$alkoxy, $C_1$–$C_4$alkylthio or by $C_1$–$C_4$alkylsulfonyl; $C_2$–$C_{12}$alkenyl; $C_2$–$C_{12}$alkynyl; $C_1$–$C_{12}$haloalkyl or a group NR$_{11}$R$_{12}$, wherein $R_{11}$ and $R_{12}$ are each independently of the other $C_1$–$C_6$alkyl, or together are tetramethylene or pentamethylene;

$R_2$ is hydrogen; and $R_3$ is $C_1$–$C_8$alkyl; $C_1$–$C_8$alkyl substituted by hydroxy, $C_1$–$C_4$alkoxy, mercapto or by $C_1$–$C_4$-alkylthio; $C_3$–$C_8$alkenyl; $C_3$–$C_8$alkynyl or $C_3$–$C_8$cycloalkyl-$C_1$–$C_4$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl;

$R_9$ is a $C_1$–$C_6$alkyl, $C_3$–$C_6$alkenyl or $C_3$–$C_6$alkynyl group substituted by one or more halogen atoms; or a group

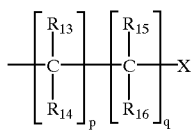

wherein p is the number one; and q is the number zero; and $R_{13}$ and $R_{14}$ are identical or different and are each independently of the other hydrogen or $C_1$–$C_4$alkyl; and X is phenyl unsubstituted or substituted by halogen, nitro, cyano, $C_1$–$C_4$alkyl or by $C_1$–$C_4$-alkoxy; cyano or —COR$_{19}$ and wherein $R_{18}$ is hydrogen or $C_1$–$C_4$alkyl (sub-group Ca).

An important sub-group is formed by compounds of formula I wherein n is the number one;

$R_1$ is $C_1$–$C_{12}$alkyl that is unsubstituted or may be substituted by $C_1$–$C_4$alkoxy, $C_1$–$C_4$alkylthio or by $C_1$–$C_4$alkylsulfonyl; $C_2$–$C_{12}$alkenyl; $C_2$–$C_{12}$alkynyl; $C_1$–$C_{12}$haloalkyl or a group NR$_{11}$R$_{12}$, wherein $R_{11}$ and $R_{12}$ are each independently of the other $C_1$–$C_6$alkyl, or together are tetramethylene or pentamethylene;

$R_2$ is hydrogen; and $R_3$ is $C_1$–$C_8$alkyl; $C_1$–$C_8$alkyl substituted by hydroxy, $C_1$–$C_4$alkoxy, mercapto or by $C_1$–$C_4$-alkylthio; $C_3$–$C_8$alkenyl; $C_3$–$C_8$alkynyl or $C_3$–$C_8$cycloalkyl-$C_1$–$C_4$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl;

$R_9$ is a $C_1$–$C_6$alkyl or $C_3$–$C_6$alkenyl group substituted by one or more halogen atoms; or a group

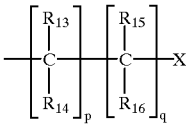

wherein p is the number one; and q is the number zero; and $R_{13}$ and $R_{14}$ are hydrogen; and X is phenyl; cyano or —COR$_{18}$ and wherein $R_{18}$ is hydrogen or $C_1$–$C_4$alkyl (sub-group Cb).

A preferred sub-group is formed by compounds of formula I wherein n is the number one;

$R_1$ is $C_1$–$C_6$alkyl; $C_2$–$C_4$alkenyl; $C_1$–$C_6$haloalkyl or a group NR$_{11}$R$_{12}$, wherein $R_{11}$ and $R_{12}$ are each independently of the other $C_1$–$C_2$alkyl;

$R_2$ is hydrogen; and $R_3$ is $C_2$–$C_5$alkyl;

$R_4$ is hydrogen or $C_1$–$C_4$alkyl;

$R_5$, $R_6$ and $R_7$ are hydrogen;

$R_8$ is $C_1$–$C_2$alkyl;

$R_9$ is a $C_1$–$C_6$alkyl or $C_3$–$C_6$alkenyl group substituted by one or more halogen atoms; or a group

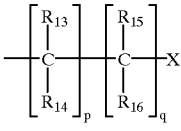

wherein p is the number one; and q is the number zero; and

9

$R_{13}$ and $R_{14}$ are hydrogen; and
X is phenyl; cyano or —$COR_{18}$ and
wherein
$R_{18}$ is hydrogen or $C_1$–$C_4$alkyl (sub-group Cd).

To be mentioned preferably are compounds of sub-group Cd wherein
n is the number one;
$R_1$ is $C_2$–$C_4$alkyl or dimethylamino;
$R_2$ is hydrogen; and
$R_3$ is $C_3$–$C_4$alkyl;
$R_4$, $R_5$, $R_6$ and $R_7$ are hydrogen;
$R_8$ is methyl;
$R_9$ is a $C_1$–$C_6$alkyl or $C_3$–$C_6$alkenyl group substituted by one or more halogen atoms; or a group

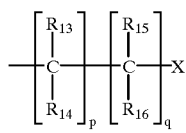

wherein
p is the number one; and
q is the number zero; and
$R_{13}$ and $R_{14}$ are hydrogen; and
X is phenyl; cyano or —$COR_{18}$ and
wherein
$R_{19}$ is hydrogen or $C_1$–$C_4$alkyl (sub-group Ce).

In the above formula I, "halogen" includes fluorine, chlorine, bromine and iodine.

The alkyl, alkenyl and alkynyl radicals may be straight-chain or branched, this applying also to the alkyl, alkenyl or alkynyl moiety of other groups containing alkyl, alkenyl or alkynyl.

Depending on the number of carbon atoms mentioned, alkyl on its own or as part of another substituent is to be understood as meaning, for example, methyl, ethyl, propyl, butyl, pentyl and the isomers thereof, such as isopropyl, isobutyl, tert-butyl or sec-butyl. Cycloalkyl denotes, depending on the number of carbon atoms mentioned, cyclopropyl, cyclobutyl, cyclopentyl, cyclohexyl, cycloheptyl or cyclooctyl.

A haloalkyl group may have one or more (identical or different) halogen atoms, such as, for example, $CHCl_2$, $CH_2F$, $CCl_3$, $CH_2Cl$, $CHF_2$, $CF_3$, $CH_2CH_2Br$, $C_2C_{15}$, $CH_2Br$, CHBrCl etc.

As a result of the presence of at least one asymmetric carbon atom and/or at least one asymmetric sulfur atom in the compounds of formula I the compounds may occur in the form of optical isomers. Owing to the presence of an aliphatic —C=C— double bond, geometrical isomerism may also occur. Formula I is intended to encompass all of those possible isomeric forms and mixtures thereof.

Certain α-amino acid derivatives having a different kind of structure have already been proposed for the control of plant-destructive fungi (for example in EP-398 072, EP-425 925, DE-40 26 966, EP-477 639, EP-493 683, DE-40 35 851, EP-487 154, EP-496 239, EP-550 788 and EP-554 729). Those compositions are not, however, satisfactory in their action. Surprisingly, with the compound structure of formula I, new kinds of microbicides having a high activity have been found.

10

DESCRIPTION OF THE PROCESS FOR THE PREPARATION OF COMPOUNDS ACCORDING TO THE INVENTION

The compounds of formula I can be prepared
a) by reaction of a substituted amino acid of formula II

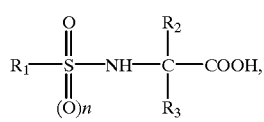

wherein the radicals $R_1$, $R_2$ and $R_3$ and n are as defined above, or their carboxy-activated derivatives, in the absence or presence of a catalyst, in the absence or presence of an acid-binding agent and in the absence or presence of a diluent, with an amine of formula III

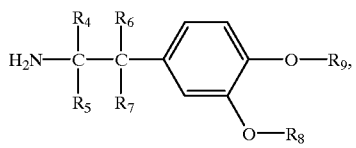

wherein $R_4$, $R_5$, $R_6$, $R_7$, $R_8$ and $R_9$ are as defined above.

The amino acid derivatives of formula II required to carry out Process a) according to the invention are known per se or can be prepared by Process aa) described below.

The amines of formula III are generally known compounds of organic chemistry.

Any carboxy-activated derivatives are suitable as carboxy-activated derivatives of the amino acid of formula II, such as acid halides, for example acid chlorides; symmetrical or mixed anhydrides, for example the mixed O-alkylcarboxylic acid anhydrides; activated esters, for example p-nitrophenyl esters or N-hydroxysuccinimide esters, and activated forms of the amino acid produced in situ using condensation agents (e.g. dicyclohexylcarbodiimide, carbonyldiimidazole, O-(benzotriaz-1-yl)-N,N,N',N'-bis(pentamethylene) uronium hexafluorophosphate, O-(benzotriaz-1-yl)-N,N,N', N'-bis(tetramethylene)uronium hexafluorophosphate, (benzotriazol-1-yloxy)-tripyrrolidinophosphonium hexafluorophosphate, (benzotriazol-1-yloxy)-tris (dimethylamino)phosphonium hexafluorophosphate or O-(benzotriazol-1-yl)-N,N,N',N'-tetramethyluronium hexafluorophosphate).

The acid halides corresponding to the amino acid of formula II can be prepared by reacting the amino acid of formula II in a manner known per se with a halogenating agent, for example phosphorus pentachloride, thionyl chloride or oxalyl chloride.

The mixed anhydrides corresponding to the amino acid of formula II can be prepared by reacting the amino acid of formula II with chloroformic acid esters, for example chloroformic acid alkyl esters, preferably chloroformic acid isobutyl ester, in the absence or presence of an acid-binding agent, such as an inorganic or organic base, for example a tertiary amine, e.g. triethylamine, pyridine, N-methylpiperidine or N-methylmorpholine.

The reaction of the amino acid of formula II, or of the carboxy-activated derivatives of the amino acid of formula II, with an amine of formula HI takes place in an inert diluent. There may be mentioned as examples: aromatic, non-aromatic or halogenated hydrocarbons, for example chlorinated hydrocarbons, e.g. methylene chloride or toluene; ketones, e.g. acetone; esters, e.g. ethyl acetate; amides, e.g. dimethylformamide; nitriles, e.g. acetonitlile; or ethers, e.g. tetrahydrofuran, dioxane, diethyl ether or tert-butyl methyl ether; or water or mixtures of those inert diluents. Examples of acid-binding agents which may be present are inorganic and organic bases, for example an alkali metal or alkaline earth metal hydroxide or carbonate, e.g. sodium hydroxide, potassium hydroxide, sodium carbonate or potassium carbonate, or, for example, a tertiary amine, e.g. triethylamine, pyridine, N-methylpiperidine or N-methylmorpholine. The temperatures are from –80 to +150° C., preferably from –40 to +40° C.

Compounds of formula I can also be prepared b) by oxidation of a compound of formula I'

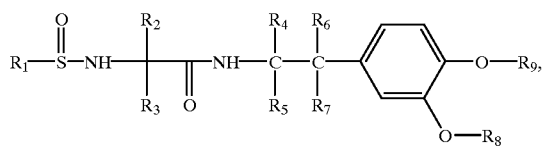

(I')

wherein $R_1$, $R_2$, $R_3$, $R_4$, $R_5$, $R_6$, $R_7$, $R_8$ and R are as defined above, with the proviso that none of the substituents $R_1$, $R_2$ and $R_3$ contains a thiol or alkylthio group.

Both organic oxidising agents, such as alkyl hydroperoxides, for example cumyl hydroperoxide, and inorganic oxidising agents, such as peroxides, for example hydrogen peroxide, or transition metal oxides, for example chromium trioxide, and transition metal oxide salts, for example potassium permanganate, potassium or sodium dichromate, are suitable oxidising agents.

The reaction of the compounds of formula I' with the oxidising agents takes place in an inert diluent, such as water or a ketone, for example acetone, or in mixtures thereof, in the absence or presence of an acid or in the absence or presence of a base, at temperatures of from –80 to +150° C.

The compounds of formula I can also be prepared c) by reaction of a compound of formula I"

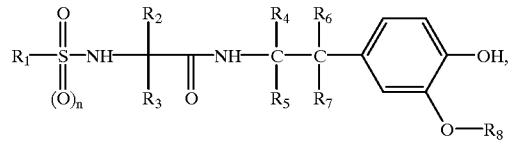

(I")

wherein $R_1$, $R_2$, $R_3$, $R_4$, $R_5$, $R_6$, $R_7$ and $R_8$ are as defined above, with a compound of formula VI

Y—$R_9$ (VI)

wherein $R_9$ is as defined above, and wherein Y is a leaving group. Suitable leaving groups are halides, for example chlorides or bromides, or sulfonates, for example tosylates, mesylates or triflates.

The reaction of the compounds of formula I" with compounds of formula VI takes place in an inert diluent. There may be mentioned as examples: aromatic, non-aromatic or halogenated hydrocarbons, for example methylene chloride or toluene; ketones, e.g. acetone; esters, e.g. ethyl acetate; amides, e.g. dimethylformamide; nitrites, e.g. acetonitrile; ethers, e.g. tetrahydrofuran, dioxane, diethyl ether or tert-butyl methyl ether; alcohols, e.g. methanol, ethanol, n-butanol, isopropanol or tert-butanol; or water; or mixtures of those inert diluents.

The reaction of the compounds of formula I" with compounds of formula VI takes place in the absence or presence of an acid-binding agent. Suitable acid-binding agents are inorganic or organic bases, for example alkali metal or alkaine earth metal hydroxides, alcoholates or carbonates, e.g. sodium hydroxide, potassium hydroxide, sodium methanolate, potassium methanolate, sodium ethanolate, potassium ethanolate, sodium tert-butanolate, potassium tert-butanolate, sodium carbonate or potassium carbonate. The temperatures are from –80 to +200° C., preferably from 0 to +120° C.

aa) The amino acid derivatives of formula II required can be prepared by reaction of an amino acid of formula VII

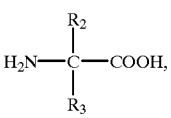

VII wherein $R_2$ and $R_3$ are as defined above, with a sulfonic acid or sulfinic acid or a sulfonic or sulfinic acid derivative of formula IV

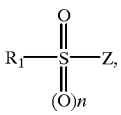

IV wherein $R_1$ and n are as defined above, and wherein Z is an OH group or a leaving group, respectively.

The sulfonic acid or sulfinic acid or the sulfonic or sulfinic acid derivative of formula IV and the amino acids of formula VI required for Process aa) are known per se.

Suitable sulfonic or sulfinic acid derivatives of formula IV are any compounds wherein Z is a leaving group, such as sulfonic acid halides or sulfinic acid halides, e.g. sulfochlorides or sulfinic acid chlorides; symmetrical or mixed anhydrides; and activated forms of sulfonic acid or sulfinic acid produced in situ using condensation agents, such as dicyclohexylcarbodiimide or carbonyldiimidazole.

The reaction of the sulfonic acid or sulfinic acid or of the sulfonic or sulfinic acid derivative of formula IV with an amine of formula V takes place in an inert diluent. There may be mentioned as examples: aromatic, non-aromatic or halogenated hydrocarbons, for example chlorinated hydrocarbons, e.g. methylene chloride or toluene; ketones, e.g. acetone; esters, e.g. ethyl acetate; amides, e.g. dimethylformamide; nitriles, e.g. acetonitrile; or ethers, e.g. tetrahydrofuran, dioxane, diethyl ether or tert-butyl methyl ether; or water or mixtures of those inert diluents. Examples of acid-binding agents which may be present are inorganic or organic bases, for example an alkali metal or alkaline earth metal hydroxide or carbonate, e.g. sodium hydroxide, potassium hydroxide, sodium carbonate or potassium carbonate, or, for example, a tertiary amine, e.g. triethylamine, pyridine, N-methylpiperidine or N-methylmorpholine. The temperatures are from −80 to +150° C., preferably from −20 to +60° C.

The compounds of formula I are stable oils or solids at room temperature that are distinguished by having valuable microbicidal properties. They can be used in the agricultural sector or related fields preventively and curatively for the control of plant-destructive microorgariisms. The compounds of formula I according to the invention are distinguished at low rates of concentration not only by outstanding microbicidal, especially fungicidal, activity but also by being especially well tolerated by plants.

Surprisingly, it has now been found that compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy pests occurring on various crops of useful plants or on parts of such plants (fruit, blossom, leaves, stems, tubers, roots), while parts of the plants which grow later, for example, also remain protected against phytopathogenic fungi.

The novel compounds of formula I prove to be preferentially effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Bremia, Pythium, Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredients, especially plant-protecting compositions, and to the use thereof in the agricultural sector or related fields.

In addition, the present invention includes the preparation of those compositions, wherein the active ingredient is homogeneously mixed with one or more of the substances or groups of substances herein described. Also included is a method for the treatment of plants which comprises applying the novel compounds of formula I or the novel compositions.

Target crops to be protected within the scope of this invention comprise, for example, the following species of plants: cereals (wheat, barley, rye, oats, rice, maize, sorghum, spelt, triticale and related species); beet (sugar beet and fodder beet); pomes, stone fruit and soft fruit (apples, pears, plums, peaches, almonds, cherries, strawberries, raspberries and blackberries); leguminous plants (beans, lentils, peas and soybeans); oil plants (rape, mustard, poppy, olives, sunflowers, coconut, castor oil plants, cocoa beans and groundnuts); cucumber plants (marrows, cucumbers and melons); fibre plants (cotton, flax, hemp and jute); citrus fruit (oranges, lemons, grapefruit and mandarins); vegetables (spinach, lettuce, asparagus, cabbages, carrots, onions, tomatoes, potatoes and paprika); lauraceae (avocados, cinnamon and camphor) and plants such as tobacco, nuts, coffee. sugar cane, tea, pepper, vines, hops, bananas and natural rubber plants, and also ornamentals.

The compounds of formula I are normally applied in the form of compositions and can be applied to the area or plant to be treated simultaneously or in succession with further active ingredients. Those further active ingredients may be fertilisers, micronutrient donors or other preparations that influence plant growth. It is also possible to use selective herbicides, and insecticides, fungicides, bactericides, nematicides, molluscicides or mixtures of several of those preparations, if desired together with further carriers, surfactants or other application-promoting adjuvants customarily employed in formulation technology.

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilisers.

A preferred method of applying a compound of formula I, or an agrochemical composition comprising at least one of those compounds, is application to the foliage of the plants (foliar application), the frequency and the rate of application depending upon the risk of infestation by the pathogen in question. The compounds of formula I may also be applied to propagation material (grains, fruits, tubers, shoots, cuttings, roots etc.) (dressing), for example either by impregnating cereal grains (seeds) or potato tubers or freshly cut shoots with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare, preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; and water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, such as pumice, broken brick, sepiolite or bentonite; and suitable nonsorbent carriers are calcite or sand. In addition, a great number of granulated materials of an inorganic nature, such as dolomite, or pulverised plant residues can be used.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Examples of non-ionic surfactants that may be mentioned are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals.

Further surfactants customarily employed in formulation technology are known to one skilled in the art or can be found in the relevant specialist literature.

The agrochemical compositions usually comprise 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further adjuvants, such as stabilisers, antifoams, viscosity regulators, binders and tackifiers, as well as fertilisers, micronutrient donors or other preparations that influence plant growth for obtaining special effects.

The Examples which follow illustrate the invention described above, without limiting the scope thereof in any way. Temperatures are given in degrees Celsius.

PREPARATION EXAMPLES FOR THE COMPOUNDS OF FORMULA I

P-1.1.: (S)-2-(Ethylsulfonylamino)-3-methyl-butyric acid N-[2-(4-benzyloxy-3-methoxyphenyl)-ethyl]-amide [Comp. 1.1]

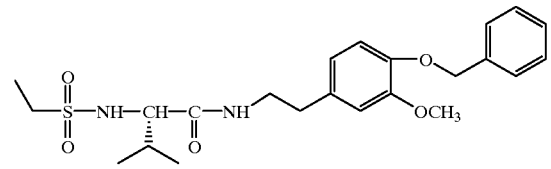

21.1 g of (S)-2-(ethylsulfonylamino)-3-methyl-butyric acid and 12 ml of N-methylmorpholine are cooled in 450 ml of tetrahydrofuran, with stirring, to −20° C. 13.2 ml of chloroformic acid isobutyl ester are added dropwise thereto over 10 min and the reaction mixture is subsequently stirred for 1 hour at −10° C. It is then cooled to −20° C. and a solution of 26.1 g of 2-(4-benzyloxy-3-methoxyphenyl)-ethylamine in 100 ml of tetrahydrofuran is added dropwise over 20 min. The reaction mixture is then stirred for 4 hours without cooling, the internal temperature gradually rising to room temperature. The reaction mixture is introduced into 400 ml of 2N hydrochloric acid and extracted twice with 500 ml of ethyl acetate each time. The organic phases are washed once with 250 ml of 2N hydrochloric acid, once with 250 ml of saturated sodium chloride solution, twice with 250 ml of 2N potassium hydrogen carbonate solution each time and once with 250 ml of saturated sodium chloride solution, dried over magnesium sulfate and concentrated, yielding (S)-2-(ethylsulfonylamino)-3-methyl-butyric acid N-[2-(4-benzyloxy-3-methoxyphenyl)-ethyl]-amide, which can be purified by recrystallisation from tert-butyl methyl ether, m.p. 140–142° C.

The compounds given in Table 1 can be obtained analogously to that Example.

TABLE 1

I

| Comp. No. | n | R₁ | R₂ | R₃ | R₈ | R₉ | Conf. α-C | Phys. data m.p. °C. |
|---|---|---|---|---|---|---|---|---|
| 1.1 | 1 | ethyl | H | 2-propyl | methyl | benzyl | (S) | 140–142 |
| 1.2 | 1 | methyl | H | 2-propyl | methyl | benzyl | (R,S) | |
| 1.3 | 1 | propyl | H | 2-propyl | methyl | benzyl | (S) | 131–135 |
| 1.4 | 1 | butyl | H | 2-propyl | methyl | benzyl | (S) | |
| 1.5 | 1 | decyl | H | 2-propyl | methyl | benzyl | (S) | |
| 1.6 | 1 | CF₃ | H | 2-propyl | methyl | benzyl | (S) | |
| 1.7 | 1 | CH₂Cl | H | 2-propyl | methyl | benzyl | (S) | |
| 1.8 | 1 | 3-chloro-propyl | H | 2-propyl | methyl | benzyl | (S) | 162–164 |
| 1.9 | 1 | methane-sulfonyl-methyl | H | 2-propyl | methyl | benzyl | (S) | |
| 1.10 | 1 | ethenyl | H | 2-propyl | methyl | benzyl | (S) | |
| 1.11 | 1 | NMe₂ | H | 2-propyl | methyl | benzyl | (S) | 121–123 |
| 1.12 | 1 | NEt₂ | H | 2-propyl | methyl | benzyl | (S) | |
| 1.13 | 1 | NH₂ | H | 2-propyl | methyl | benzyl | (S) | |
| 1.14 | 1 | N-pyrro-lidine | H | 2-propyl | methyl | benzyl | (S) | |
| 1.15 | 0 | i-propyl | H | 2-propyl | methyl | benzyl | (S) | |
| 1.16 | 0 | cyclo-hexyl | H | 2-propyl | methyl | benzyl | (S) | |
| 1.17 | 1 | ethyl | H | 2-butyl | methyl | benzyl | (S) | |
| 1.18 | 1 | ethyl | H | 1-(tert-butyl)-oxy-ethyl | methyl | benzyl | (S) | |
| 1.19 | 1 | ethyl | H | ethyl | methyl | benzyl | (S) | |
| 1.20 | 1 | NMe₂ | H | ethyl | methyl | benzyl | (S) | |
| 1.21 | 1 | ethyl | H | 2-Me-propyl | methyl | benzyl | (S) | |
| 1.22 | 1 | ethyl | H | 2-(CH₃S)ethyl | methyl | benzyl | (S) | |
| 1.23 | 1 | ethyl | H | 1-(OH)-ethyl | methyl | benzyl | (S) | |
| 1.24 | 1 | methyl | CH₃ | methyl | methyl | benzyl | — | |
| 1.25 | 1 | methyl | —(CH₂)₄— | | methyl | benzyl | — | |
| 1.26 | 1 | ethyl | CH₃ | methyl | methyl | benzyl | — | |
| 1.27 | 1 | ethyl | —(CH₂)₄— | | methyl | benzyl | — | |
| 1.28 | 1 | ethyl | H | 2-propyl | ethyl | benzyl | (S) | |
| 1.29 | 1 | ethyl | H | 2-propyl | methyl | phenyl | (S) | 135–137 |
| 1.30 | 1 | ethyl | H | 2-propyl | methyl | 4-CH₃O—phenyl | (S) | |
| 1.31 | 1 | NMe₂ | H | 2-propyl | methyl | phenyl | (S) | resin |
| 1.32 | 1 | methyl | H | 2-propyl | methyl | benzyl | (S) | 139–142 |
| 1.33 | 1 | 2-propyl | H | 2-propyl | methyl | benzyl | (S) | 113–119 |

P-2: (S)-2-(Ethylsulfonylamino)-3-methyl-butyric acid N-[2-(4-hydroxy-3-methoxyphenyl)-ethyl]-amide

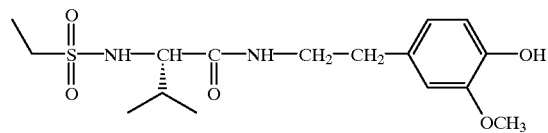

a) 5.1 g of (S)-2-(ethylsulfonylamino)-3-methyl-butyric acid and 5.7 ml of N-methylmorpholine are cooled in 200 ml of tetrahydrofuran, with stirring, to −20° C. 3.15 ml of chloroformic acid isobutyl ester are added dropwise thereto. Stirring is then carried out for 30 min, during which the reaction temperature is increased to −10° C. Cooling is then carried out to −20° C. again and 5.0 g of 2-(4-hydroxy-3-methoxyphenyl)-ethylamine hydrochloride are introduced. The reaction mixture is allowed to warm to room temperature and is stirred for a further 24 hours. The reaction mixture is introduced into 300 ml of 2N hydrochloric acid. It is extracted twice with 500 ml of ethyl acetate each time. The organic phases are washed twice with 100 ml of saturated sodium chloride solution each time, combined, dried over magnesium sulfate and concentrated. The residue is purified by flash-chromatography on silica gel using a mixture of ethyl acetate/n-hexane 3:1, yielding (S)-2-(ethylsulfonylamino)-3-methyl-butyric acid N-[2-(4-hydroxy-3-methoxyphenyl)ethyl]-amide in the form of a colourless oil.

b) 14.5 g of (S)-2-(ethylsulfonylamino)-3-methyl-butyric acid N-[2-(4-benzyloxy-3-methoxyphenyl)-ethyl]-amide (Ex. P-1. 1) are dissolved in 420 ml of tetrahydrofuran and shaken together with 3 g of palladium-on-carbon (5%) in a duck-shaped hydrogenation vessel for 5 hours in a hydrogen atmosphere at normal pressure. The catalyst is then removed by filtration. The filtrate is concentrated. The residue is purified by flash-chromatography on silica gel using ethyl acetate/n-hexane 3:1, yielding (S)-2-(ethylsulfonylamino)-3-methyl-butyric acid N-[2-(4-hydroxy-3-methoxyphenyl) ethyl]-amide in the form of a colourless oil.

c) A mixture of 2.1 g of (S)-2-(ethylsulfonylamino)-3-methyl-butyric acid, 1.7 g of 2-(4-hydroxy-3-methoxyphenyl)-ethylamine, 4.6 g of (benzotriazol-1-yloxy)-tris(dimethylamino)phosphonium hexafluorophosphate (BOP) and 4.5 ml of N,N-diisopropylethylamine is stirred in 40 ml of N,N-dimethylformamide at room temperature for 2 hours. The reaction mixture is introduced into 500 ml of water and extracted twice with 400 ml of ethyl acetate each time. The organic phases are washed once with 300 ml of water and once with 200 ml of saturated sodium chloride solution, dried over magnesium sulfate and concentrated. (S)-2-(Ethylsulfonylamino)-3-methyl-butyric acid N-[2-(4-hydroxy-3-methoxyphenyl)-ethyl]-amide is obtained in the form of an oil, which can be purified by flash-chromatography on silica gel using a mixture of ethyl acetate/n-hexane=3:1.

TABLE 2

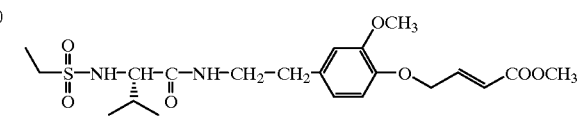

| Comp. No. | $R_1$ | Physical data |
|---|---|---|
| 2.1 | ethyl | oil |
| 2.2 | methyl | m.p. 149–151° C. |

TABLE 2-continued

| Comp. No. | $R_1$ | Physical data |
|---|---|---|
| 2.3 | propyl | oil |
| 2.4 | 2-propyl | oil |
| 2.5 | 3-chloropropyl | m.p. 124–126° C. |

P-3.12: (S)-2-(Ethylsulfonylamino)-3-methyl-butyric acid N-{2-[4-(3-methoxycarbonylprop-2-en-1-yl)-oxy-3-methoxyphenyl]-ethyl}-amide A mixture of 2.4 g of (S)-2-(ethylsulfonylamino)-3-methyl-butyric acid N-[2-(4-hydroxy-3-methoxyphenyl)-ethyl]-amide, 1.2 ml of 4-bromo-but-2-enoic acid and 9.1 ml of a 1.1M sodium methanolate solution in methanol (prepared beforehand by dissolving 44 g of sodium in 1 liter of methanol) and 30 ml of methanol is heated under reflux for 4 hours. When the reaction mixture has cooled it is introduced into 300 ml of water and extracted twice with 300 ml of ethyl acetate each time. The organic phases are washed twice with 100 ml of saturated sodium chloride each time, dried over magnesium sulfate and concentrated, yielding (S)-2-(ethylsulfonylamino)-3-methyl-butyric acid N-{2-[4-(3-methoxycarbonyl-prop-2-en-1-yl)-oxy-3-methoxyphenyl]ethyl}-amide in the form of an oil, which can be further purified by chromatography on silica gel using ethyl acetate.

The compounds listed in Table 3 can be obtained in an analogous manner.

TABLE 3

| Comp. No. | $R_1$ | $R_2$ | $R_3$ | $R_8$ | $R_9$ | Conf. α-C | Phys. data m.p. °C. |
|---|---|---|---|---|---|---|---|
| 3.1 | ethyl | H | 2-propyl | methyl | $CH_2$—CN | (S) | |
| 3.2 | ethyl | H | 2-propyl | methyl | $CH_2$—CN | (R,S) | |
| 3.3 | ethyl | H | 2-butyl | methyl | $CH_2$—CN | (S) | |
| 3.4 | ethyl | H | ethyl | methyl | $CH_2$—CN | (S) | |
| 3.5 | ethyl | H | ethyl | methyl | $CH_2$—CN | (R,S) | |
| 3.6 | methyl | H | 2-propyl | methyl | $CH_2$—CN | (S) | |
| 3.7 | propyl | H | 2-propyl | methyl | $CH_2$—CN | (S) | |
| 3.8 | butyl | H | 2-propyl | methyl | $CH_2$—CN | (S) | |
| 3.9 | 3-Cl-propyl | H | 2-propyl | methyl | $CH_2$—CN | (S) | |

TABLE 3-continued

[Structure: R₁—S(O)₂—NH—C(R₂)(R₃)—C(O)—NH—CH₂CH₂—(phenyl with O—R₈ and O—R₉ substituents)]

| Comp. No. | R₁ | R₂ | R₃ | R₈ | R₉ | Conf. α-C | Phys. data m.p. ° C. |
|---|---|---|---|---|---|---|---|
| 3.10 | NMe₂ | H | 2-propyl | methyl | CH₂—CN | (S) | |
| 3.11 | ethyl | CH₃ | methyl | methyl | CH₂—CN | (S) | |
| 3.12 | ethyl | H | 2-propyl | methyl | CH₂—CH=CH—COOCH₃ | (S) | oil |
| 3.13 | NMe₂ | H | 2-propyl | methyl | CH₂—CH=CH—COOCH₃ | (S) | |
| 3.14 | ethyl | H | 2-propyl | methyl | CH₂—CH=CH—COOEt | (S) | |
| 3.15 | NMe₂ | H | 2-propyl | methyl | CH₂—CH=CH—COOEt | (S) | |
| 3.16 | ethyl | H | 2-propyl | methyl | CH₂—CH=CHCl | (S) | 120–129 |
| 3.17 | NMe₂ | H | 2-propyl | methyl | CH₂—CH=CHCl | (S) | |
| 3.18 | ethyl | H | 2-propyl | methyl | CH₂—C(Cl)=CH₂ | (S) | 128–130 |
| 3.19 | NMe₂ | H | 2-propyl | methyl | CH₂—C(Cl)=CH₂ | (S) | |
| 3.20 | ethyl | H | 2-propyl | methyl | CH₂—CH=C(CH₃)Cl | (S) | |
| 3.21 | NMe₂ | H | 2-propyl | methyl | CH₂—CH=C(CH₃)Cl | (S) | |
| 3.22 | ethyl | H | 2-propyl | methyl | CH₂—CH=CHBr | (S) | |
| 3.23 | NMe₂ | H | 2-propyl | methyl | CH₂—CH=CHBr | (S) | |
| 3.24 | ethyl | H | 2-propyl | methyl | CH₂—CH=CCl₂ | (S) | |
| 3.25 | NMe₂ | H | 2-propyl | methyl | CH₂—CH=CCl₂ | (S) | |
| 3.26 | ethyl | H | 2-propyl | methyl | CH₂—C(Cl)=CHCl | (S) | |
| 3.27 | NMe₂ | H | 2-propyl | methyl | CH₂—C(Cl)=CHCl | (S) | |
| 3.28 | ethyl | H | 2-propyl | methyl | CH₂CH₂CH₂—COOCH₃ | (S) | |
| 3.29 | NMe₂ | H | 2-propyl | methyl | CH₂CH₂CH₂—COOCH₃ | (S) | |
| 3.30 | ethyl | H | 2-propyl | methyl | CH₂CH₂CH₂—COOEt | (S) | |
| 3.31 | NMe₂ | H | 2-propyl | methyl | CH₂CH₂CH₂—COOEt | (S) | |
| 3.32 | ethyl | H | 2-propyl | ethyl | CH₂—CN | (S) | |
| 3.33 | ethyl | H | 2-propyl | allyl | CH₂—CN | (S) | |
| 3.34 | ethyl | H | 2-propyl | methyl | CH(CH₃)—CN | (S) | |
| 3.35 | NMe₂ | H | 2-propyl | methyl | CH(CH₃)—CN | (S) | |
| 3.36 | ethyl | H | 2-propyl | methyl | CH₂—COOCH₃ | (S) | |
| 3.37 | NMe₂ | H | 2-propyl | methyl | CH₂—COOCH₃ | (S) | |
| 3.38 | ethyl | H | 2-propyl | methyl | CH₂—COOEt | (S) | |
| 3.39 | NMe₂ | H | 2-propyl | methyl | CH₂—COOEt | (S) | |
| 3.40 | ethyl | H | 2-propyl | methyl | CH(CH₃)—COOCH₃ | (S) | |
| 3.41 | NMe₂ | H | 2-propyl | methyl | CH(CH₃)—COOCH₃ | (S) | |
| 3.42 | ethyl | H | 2-propyl | methyl | CH(CH₃)—COOEt | (S) | |
| 3.43 | NMe₂ | H | 2-propyl | methyl | CH(CH₃)—COOEt | (S) | |
| 3.44 | ethyl | H | 2-propyl | methyl | o-bromobenzyl | (S) | |
| 3.45 | NMe₂ | H | 2-propyl | methyl | o-bromobenzyl | (S) | |
| 3.46 | ethyl | H | 2-propyl | methyl | p-bromobenzyl | (S) | |
| 3.47 | NMe₂ | H | 2-propyl | methyl | p-bromobenzyl | (S) | |
| 3.48 | ethyl | H | 2-propyl | methyl | o-cyanobenzyl | (S) | 164–167 |
| 3.49 | NMe₂ | H | 2-propyl | methyl | o-cyanobenzyl | (S) | |
| 3.50 | ethyl | H | 2-propyl | methyl | p-cyanobenzyl | (S) | |
| 3.51 | NMe₂ | H | 2-propyl | methyl | p-cyanobenzyl | (S) | |
| 3.52 | ethyl | H | 2-propyl | methyl | p-methylbenzyl | (S) | 146–148 |
| 3.53 | NMe₂ | H | 2-propyl | methyl | p-methylbenzyl | (S) | |
| 3.54 | ethyl | H | 2-propyl | methyl | o-chlorobenzyl | (S) | 136–138 |
| 3.55 | NMe₂ | H | 2-propyl | methyl | o-chlorobenzyl | (S) | |
| 3.56 | ethyl | H | 2-propyl | methyl | m-chlorobenzyl | (S) | 131–134 |
| 3.57 | NMe₂ | H | 2-propyl | methyl | m-chlorobenzyl | (S) | |
| 3.58 | ethyl | H | 2-propyl | methyl | p-chlorobenzyl | (S) | 138–140 |
| 3.59 | NMe₂ | H | 2-propyl | methyl | p-chlorobenzyl | (S) | |
| 3.60 | ethyl | H | 2-propyl | methyl | o-CF₃-benzyl | (S) | |
| 3.61 | NMe₂ | H | 2-propyl | methyl | o-CF₃-benzyl | (S) | |
| 3.62 | ethyl | H | 2-propyl | methyl | m-CF₃-benzyl | (S) | 119–121 |
| 3.63 | NMe₂ | H | 2-propyl | methyl | m-CF₃-benzyl | (S) | |
| 3.64 | ethyl | H | 2-propyl | methyl | p-CF₃-benzyl | (S) | |
| 3.65 | NMe₂ | H | 2-propyl | methyl | p-CF₃-benzyl | (S) | |
| 3.66 | ethyl | H | 2-propyl | methyl | p-fluorobenzyl | (S) | 146–151 |
| 3.67 | NMe₂ | H | 2-propyl | methyl | p-fluorobenzyl | (S) | |
| 3.68 | ethyl | H | 2-propyl | methyl | p-methoxybenzyl | (S) | 149–152 |
| 3.69 | NMe₂ | H | 2-propyl | methyl | p-methoxybenzyl | (S) | |
| 3.70 | ethyl | H | 2-propyl | methyl | p-nitrobenzyl | (S) | 169–170 |
| 3.71 | NMe₂ | H | 2-propyl | methyl | p-nitrobenzyl | (S) | |
| 3.72 | ethyl | H | 2-propyl | methyl | 1-phenethyl | (S) | |
| 3.73 | NMe₂ | H | 2-propyl | methyl | 1-phenethyl | (S) | |
| 3.74 | ethyl | H | 2-propyl | methyl | CH₂—CO—CH₃ | (S) | |
| 3.75 | NMe₂ | H | 2-propyl | methyl | CH₂—CO—CH₃ | (S) | |

TABLE 3-continued $$R_1-\underset{\underset{O}{\overset{O}{\|}}}{S}-NH-\underset{\underset{R_3}{\overset{R_2}{|}}}{C}-\underset{\overset{\|}{O}}{C}-NH-CH_2CH_2-\underset{}{\underset{}{\text{(phenyl)}}}-\underset{O-R_9}{\overset{O-R_8}{}}$$

| Comp. No. | R₁ | R₂ | R₃ | R₈ | R₉ | Conf. α-C | Phys. data m.p. °C. |
|---|---|---|---|---|---|---|---|
| 3.76 | ethyl | H | 2-propyl | methyl | $CH_2$—CHO | (S) | |
| 3.77 | NMe₂ | H | 2-propyl | methyl | $CH_2$—CHO | (S) | |
| 3.78 | ethyl | H | 2-propyl | methyl | $CH(CH_3)$—CO—$CH_3$ | (S) | |
| 3.79 | NMe₂ | H | 2-propyl | methyl | $CH(CH_3)$—CO—$CH_3$ | (S) | |
| 3.80 | ethyl | H | 2-propyl | methyl | $CH(CH_3)$—CHO | (S) | |
| 3.81 | NMe₂ | H | 2-propyl | methyl | $CH(CH_3)$—CHO | (S) | |
| 3.82 | ethyl | H | 2-propyl | methyl | acetyl | (S) | |
| 3.83 | NMe₂ | H | 2-propyl | methyl | acetyl | (S) | |
| 3.84 | ethyl | H | 2-propyl | methyl | propionyl | (S) | |
| 3.85 | NMe₂ | H | 2-propyl | methyl | propionyl | (S) | |
| 3.86 | ethyl | H | 2-propyl | methyl | pivaloyl | (S) | |
| 3.87 | NMe₂ | H | 2-propyl | methyl | pivaloyl | (S) | |
| 3.88 | ethyl | H | 2-propyl | methyl | benzoyl | (S) | |
| 3.89 | NMe₂ | H | 2-propyl | methyl | benzoyl | (S) | |
| 3.90 | ethyl | H | 2-propyl | methyl | p-nitrobenzoyl | (S) | |
| 3.91 | NMe₂ | H | 2-propyl | methyl | p-nitrobenzoyl | (S) | |
| 3.92 | ethyl | H | 2-propyl | methyl | $COOCH_3$ | (S) | |
| 3.93 | NMe₂ | H | 2-propyl | methyl | $COOCH_3$ | (S) | |
| 3.94 | ethyl | H | 2-propyl | methyl | COOEt | (S) | |
| 3.95 | NMe₂ | H | 2-propyl | methyl | COOEt | (S) | |
| 3.96 | ethyl | H | 2-propyl | methyl | $CH_2$—CO-phenyl | (S) | |
| 3.97 | NMe₂ | H | 2-propyl | methyl | $CH_2$—CO-phenyl | (S) | |
| 3.98 | ethyl | H | 2-propyl | methyl | $CH_2$—CO—CH=$CH_2$ | (S) | |
| 3.99 | NMe₂ | H | 2-propyl | methyl | $CH_2$—CO—CH=$CH_2$ | (S) | |
| 3.100 | methyl | H | 2-propyl | methyl | 2,4-$Cl_2$-benzyl | (S) | 163–165 |
| 3.101 | methyl | H | 2-propyl | methyl | $CH_2$—CH=CHCl | (S) | 147–153 |
| 3.102 | ethyl | H | 2-propyl | methyl | 3,4-$Cl_2$-benzyl | (S) | 147–149 |

Preparation Example for Intermediates:

I-1.1: (R,S)-Methanesulfonic acid N-(2-methyl-1-carboxy)-propyl-amide

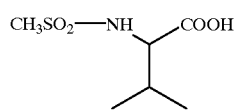

[Comp. 4.1]

30 g of D,L-valine and 10.2 g of sodium hydroxide are dissolved in 250 ml of water and cooled, with stirring, to 0° C. A solution of 10.2 g of sodium hydroxide in 250 ml of water and a solution of 20 ml of methanesulfonic acid chloride in 250 ml of toluene are simultaneously added dropwise to that solution over 1 hour. The reaction mixture is left at 0° C. for 2 hours and then stirred further for 16 hours at room temperature. The toluene phase is removed in a separating funnel and discarded. The aqueous phase is adjusted to pH <3 with conc. hydrochloric acid. Extraction is carried out twice with 100 ml of ether each time. The organic phases are washed twice with 200 ml of saturated sodium chloride solution each time, combined, dried over magnesium sulfate and concentrated, yielding (R,S)-methanesulfonic acid N-(2-methyl-1-carboxy)-propyl-amide, which can be purified by recrystallisation from ethyl acetate/hexane; m.p. 90–91° C.

The intermediates indicated in Table 4 are obtained analogously to that Example.

TABLE 4

$$R_1-\underset{\underset{(O)_n}{\overset{O}{\|}}}{S}-NH-\underset{\underset{R_3}{\overset{R_2}{|}}}{C}-COOH$$

| Comp. No. | n | R₁ | R₂ | R₃ | Conf. α-C | Phys. data m.p. °C. |
|---|---|---|---|---|---|---|
| 4.1 | 1 | methyl | H | 2-propyl | (R,S) | 90–91 |
| 4.2 | 1 | methyl | H | 2-propyl | (S) | oil |
| 4.3 | 1 | NMe₂ | H | 2-propyl | (R,S) | oil |
| 4.4 | 1 | NMe₂ | H | 2-propyl | (S) | resin |
| 4.5 | 0 | methyl | H | 2-propyl | (R,S) | |
| 4.6 | 0 | 2-propyl | H | 2-propyl | (R,S) | |
| 4.7 | 0 | 2-methyl-2-propyl | H | 2-propyl | (R,S) | |
| 4.8 | 0 | methyl | H | 2-propyl | (S) | |
| 4.9 | 0 | 2-propyl | H | 2-propyl | (S) | |
| 4.10 | 0 | 2-methyl-2-propyl | H | 2-propyl | (S) | |
| 4.11 | 0 | cyclohexyl | H | 2-propyl | (S) | |
| 4.12 | 1 | ethyl | H | 2-propyl | (S) | resin |
| 4.13 | 1 | NMe₂ | H | 2-butyl | (S) | resin |
| 4.14 | 1 | ethyl | H | 1-(tert-butyl)-oxy-ethyl | (S) | oil |
| 4.15 | 1 | methyl | H | ethyl | (S) | resin |
| 4.16 | 1 | ethyl | H | ethyl | (S) | resin |
| 4.17 | 1 | methyl | CH₃ | methyl | — | 109–111 |
| 4.18 | 1 | methyl | | tetramethylene | | |
| 4.19 | 1 | propyl | H | 2-propyl | (S) | oil |
| 4.20 | 1 | 2-propyl | H | 2-propyl | (S) | oil |

TABLE 4-continued $$R_1 - \overset{O}{\underset{(O)_n}{\overset{\|}{S}}} - NH - \overset{R_2}{\underset{R_3}{\overset{|}{C}}} - COOH$$

| Comp. No. | n | R₁ | R₂ | R₃ | Conf. α-C | Phys. data m.p. °C. |
|---|---|---|---|---|---|---|
| 4.21 | 1 | 3-chloropropyl | H | 2-propyl | (S) | 108–109 |

2. Formulation Examples for compounds of formula I (throughout, percentages are by weight)

| F-2.1. Wettable powders | a) | b) | c) |
|---|---|---|---|
| a compound of Tables 1 and 3 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of any desired concentration.

| F-2.2. Emulsifiable concentrate | |
|---|---|
| a compound of Tables 1 and 3 | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 34% |
| xylene mixture | 50% |

Emulsions of any required concentration can be obtained from this concentrate by dilution with water.

| F-2.3. Dusts | a) | b) |
|---|---|---|
| a compound of Tables 1 and 3 | 5% | 8% |
| talcum | 95% | — |
| kaolin | — | 92% |

Ready-for-use dusts are obtained by mixing the active ingredient with the carrier and grinding the mixture in a suitable mill.

| F-2.4. Extruder anules | |
|---|---|
| a compound of Tables 1 and 3 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| F-2.5. Coated anules | |
|---|---|
| a compound of Tables 1 and 3 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| F-2.6. Suspension concentrate | |
|---|---|
| a compound of Tables 1 and 3 | 40% |
| ethylene glycol | 10% |
| nonylphenol polyethylene glycol ether (15 mol of ethylene oxide) | 6% |
| sodium lignosulfonate | 10% |
| carboxymethylcellulose | |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired dilution can be obtained by dilution with water.

BIOLOGICAL EXAMPLES

B-1: Action against Plasmopara viticola on vines a) Residual-protective action

Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and 20° C.

b) Residual-curative action

Vine seedlings are infected at the 4- to 5-leaf stage with a sporangia suspension of the fungus. After incubation for 24 hours in a humidity chamber at 95–100% relative humidity and 20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 and 3 exhibit a very good fungicidal action against Plasmopara viticola on vines. Active ingredients Nos. 1.1, 1.11 and others achieve complete suppression of fungus infestation (residual infestation 0 to 5%). On the other hand, Plasmopara infestation on untreated and infected control plants is 100%.

B-2: Action against Phytophthora on tomato plants a) Residual-protective action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants which are above ground. After 4 days, the treated plants are infected with a sporangia suspension of the fungus. Fungus infestation is evaluated after incubation of the infected plants for 4 days at 90–100% relative humidity and 20° C.

Compounds of Tables 1 and 3 exhibit a lasting effect (less than 20% fungus infestation). Infestation is prevented virtually completely (0 to 5% infestation) with compounds Nos. 1.1, 1.11 and others. On the other hand, Phytophthora infestation on untreated and infected control plants is 100%.

B-3 : Action against Phytophthora on potato plants a) Residual-protective action 2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants which are above ground. After 48 hours, the treated plants are infected with a sporangia suspension of the fungus. Fungus infestation is evaluated after incubation of the infected plants for 4 days at 90–100% relative humidity and 20° C.

Compounds of Tables 1 and 3 exhibit a lasting effect (less than 20% fungus infestation). Infestation is prevented virtually completely (0 to 5% infestation) with compounds Nos. 1.1, 1.11 and others. On the other hand, Phytophthora infestation on untreated and infected control plants is 100%.

What is claimed is:

1. A compound of formula I

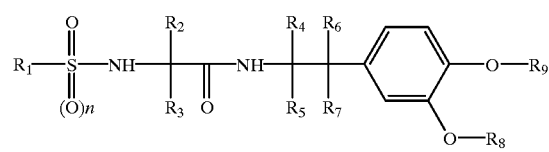

wherein the substituents are defined as follows:

n is the number zero or one;

$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or by $C_3$–$C_6$alkynyloxycarbonyl; $C_3$–$C_8$cycloalkyl; $C_2$–$C_{12}$alkenyl; $C_2$–$C_{12}$-alkynyl; $C_1$–$C_{12}$haloalkyl or a group $NR_{11}R_{12}$, wherein $R_{11}$ and $R_{12}$ are each independently of the other hydrogen or $C_1$–$C_6$alkyl, or together are tetramethylene or pentamethylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$-alkynyl or $C_3$–$C_8$cycloalkyl-$C_1$–$C_4$alkyl; or the two groups $R_2$ and $R_3$ together with the carbon atom to which they are bonded form a three- to eight-membered carbocyclic ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

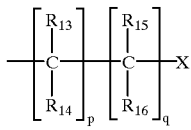

wherein p and q are identical or different and are each independently of the other the number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$Cycoalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; —$COOR_{17}$; —$COR_{18}$ or a group

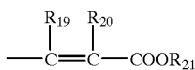

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_2$–$C_6$alkenyl, $C_2$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl.

2. A compound of formula I

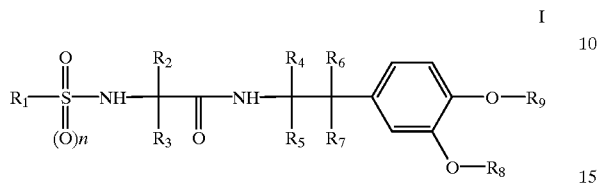

wherein the substituents are defined as follows:
n is the number zero or one;
$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or by $C_3$–$C_6$alkynyloxycarbonyl; $C_3$–$C_8$cycloalky; $C_2$–$C_{12}$alkenyl; $C_2$–$C_{12}$-alkynyl; $C_1$–$C_{12}$haloalkyl or a group $NR_{11}R_{12}$, wherein $R_{11}$ and $R_{12}$ are each independently of the other hydrogen or $C_1$–$C_6$alkyl, or together are tetramethylene or pentamethylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$-alkynyl or $C_3$–$C_8$cycloalkyl-$C_1$–$C_4$alkyl; or the two groups $R_2$ and $R_3$ together with the carbon atom to which they are bonded form a three- to eight-membered carbocyclic ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

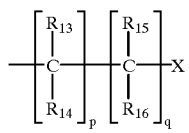

wherein
p and q are identical or different and are each independently of the other the number zero or one; and
$R_{13}$, $R_{14}$, $R_{15}$ and $R_{16}$ are identical or different and are each independently of the others hydrogen or $C_1$–$C_4$alkyl; and
X is hydrogen, in which case p and q must have the value zero; phenyl unsubstituted or substituted by halogen, nitro, cyano, $C_1$–$C_4$alkyl or by $C_1$–$C_4$alkoxy; cyano; —COOR$_{17}$; —COR$_{18}$ or a group

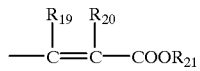

wherein
$R_{17}$ and $R_2$, are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl.

3. A compound of formula I according to claim 2, wherein
n is the number one;
$R_1$ is $C_1$–$C_{12}$alkyl that is unsubstituted or may be substituted by $C_1$–$C_4$alkoxy, $C_1$–$C_4$alkylthio or by $C_1$–$C_4$alkylsulfonyl; $C_2$–$C_{12}$alkenyl; $C_2$–$C_{12}$alkynyl; $C_1$–$C_{12}$haloalkyl or a group $NR_{11}R_{12}$, wherein $R_{11}$ and $R_{12}$ are each independently of the other hydrogen or $C_1$–$C_6$-alkyl, or together are tetramethylene or pentamethylene;
$R_2$ is hydrogen; and
$R_3$ is $C_1$–$C_8$alkyl; $C_1$–$C_8$alkyl substituted by hydroxy, $C_1$–$C_4$alkoxy, mercapto or by $C_1$–$C_4$-alkylthio; $C_3$–$C_8$alkenyl; $C_3$–$C_8$alkynyl or $C_3$–$C_8$cycloalkyl-$C_1$–$C_4$alkyl.

4. A compound of formula I according to claim 3, wherein $R_8$ is $C_1$–$C_6$alkyl.

5. A compound of formula I according to claim 4, wherein
$R_1$ is $C_1$–$C_{12}$alkyl; $C_1$–$C_{12}$haloalkyl or a group $NR_{11}R_{12}$, wherein $R_{11}$ and $R_{12}$ are $C_1$–$C_6$alkyl;
$R_3$ is $C_1$–$C_8$alkyl;
$R_4$ is hydrogen or $C_1$–$C_4$alkyl; and
$R_5$, $R_6$ and $R_7$ are hydrogen.

6. A compound of formula I according to claim 5, wherein
$R_1$ is $C_1$–$C_4$alkyl or dimethylamino;
$R_3$ is $C_3$–$C_4$alkyl;
$R_4$ is hydrogen or methyl; and
$R_8$ is $C_1$–$C_2$alkyl.

7. A compound of formula I according to claim 6, wherein
$R_1$ is $C_2$–$C_4$alkyl or dimethylamino;
$R_3$ is 2-propyl;
$R_4$ is hydrogen; and
$R_8$ is methyl.

8. A compound of formula according to claim 4, wherein
$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

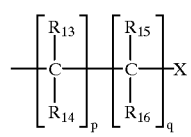

wherein
p is the number zero or one; and
q is the number zero; and
$R_{13}$ and $R_{14}$ are identical or different and are each independently of the other hydrogen or $C_1$–$C_4$alkyl; and
X is hydrogen, in which case p must have the value zero; phenyl unsubstituted or substituted by halogen, nitro, cyano, $C_1$–$C_4$alkyl or by $C_1$–$C_4$alkoxy; cyano; —COOR$_{17}$; —COR$_{18}$ or a group

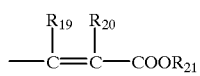

wherein $R_{17}$ and $R_{21}$ are $C_1$–$C_6$alkyl, and $R_{19}$ is hydrogen; $C_1$–$C_6$alkyl or phenyl, unsubstituted or substituted by halogen, nitro, cyano, $C_1$–$C_4$alkyl or by $C_1$–$C_4$alkoxy, and $R_{19}$ and $R_{20}$ are hydrogen.

9. A compound of formula I according to claim 8, wherein $R_9$ is a $C_1$–$C_6$alkyl, $C_3$–$C_6$alkenyl or $C_3$–$C_6$alkynyl group substituted by one or more halogen atoms; or a group

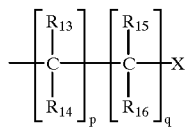

wherein p is the number one; and q is the number zero; and

X is phenyl unsubstituted or substituted by halogen, nitro, cyano, $C_1$–$C_4$alkyl or by $C_1$–$C_4$-alkoxy; cyano or —$COR_{18}$ and wherein $R_{18}$ is hydrogen or $C_1$–$C_4$alkyl.

10. A compound of formula I according to claim 9, wherein $R_9$ is a $C_1$–$C_6$alkyl or $C_3$–$C_6$alkenyl group substituted by one or more halogen atoms; or a group

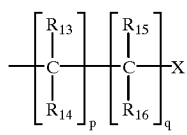

wherein p is the number one; and q is the number zero; and $R_{13}$ and $R_{14}$ are hydrogen; and X is phenyl; cyano or —$COR_{18}$.

11. A compound of formula I according to claim 10, wherein $R_1$ is $C_1$–$C_6$alkyl; $C_2$–$C_4$alkenyl; $C_1$–$C_6$haloalkyl or a group $NR_{11}R_{12}$, wherein $R_{11}$ and $R_{12}$ are each independently of the other $C_1$–$C_2$alkyl;

$R_3$ is $C_2$–$C_5$alkyl;

$R_4$ is hydrogen or $C_1$–$C_4$alkyl;

$R_5$, $R_6$ and $R_7$ are hydrogen; and $R_8$ is $C_1$–$C_2$alkyl.

12. A compound of formula I according to claim 11, wherein $R_1$ is $C_2$–$C_4$alkyl or dimethylamino;

$R_3$ is $C_3$–$C_4$alkyl;

$R_4$, $R_5$, $R_6$ and $R_7$ are hydrogen; and $R_8$ is methyl.

13. A process for the preparation of a compound of formula I according to claim 1, which comprises a) reacting a substituted amino acid of formula II

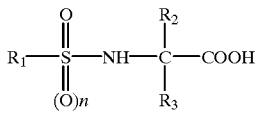

with an amine of formula III

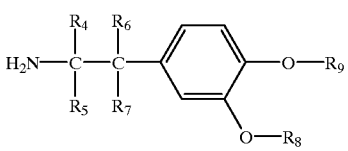

with or without a diluent, in the absence or presence of an acid-binding agent, at temperatures of from –80° C. to 150° C., or b) oxidising a compound of formula I'

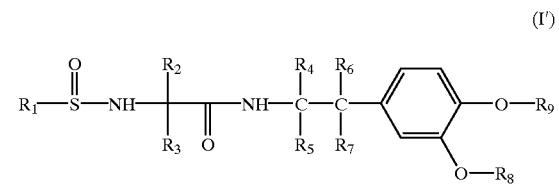

with an oxidising agent in a diluent, in the absence or presence of an acid or a base, at temperatures of from –80° C. to 150° C., or c) reacting a compound of formula I"

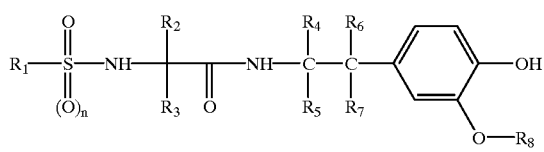

with a compound of formula VI

in a diluent, in the absence or presence of an acid-binding agent, at temperatures of from –80 to 200° C., wherein, in formulae II, III, VI, I' and I", the substituents $R_{1a, R2}$, $R_3$, $R_4$, $R_5$, $R_6$, $R_7$, $R_8$, $R_9$ and n are as defined for formula I and Y is halogen or a sulfonate.

14. A composition for controlling and preventing infestation of plants by microorganisms, which comprises as active ingredient a compound of formula I according to claim 1, together with a suitable carrier.

15. A method of controlling and preventing infestation of plants by microorganisms, which comprises applying a compound of formula I as active ingredient to the plant, to parts of the plant or to the nutrient medium of the plant.

16. A method according to claim 15, wherein phytopathogenic fungi are controlled.

17. A method according to claim 16, wherein Oomycetes are controlled.

18. A method according to claim 15, which comprises treating seed.

* * * * *